(12) United States Patent
Gupta et al.

(10) Patent No.: US 8,758,445 B2
(45) Date of Patent: *Jun. 24, 2014

(54) PROSTHETIC WRIST IMPLANT

(75) Inventors: Amitava Gupta, Louisville, KY (US);
David A. Leibel, Princeton, MN (US);
William P. Cooney, III, Rochester, MN (US)

(73) Assignee: Avanta Orthopaedics, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/398,460

(22) Filed: Feb. 16, 2012

(65) Prior Publication Data

US 2012/0150308 A1 Jun. 14, 2012

Related U.S. Application Data

(60) Continuation of application No. 12/626,578, filed on Nov. 25, 2009, now Pat. No. 8,118,876, which is a continuation of application No. 11/210,416, filed on Aug. 24, 2005, now Pat. No. 7,628,819, which is a division of application No. 10/897,317, filed on Jul. 22, 2004, now Pat. No. 7,625,408.

(60) Provisional application No. 60/489,037, filed on Jul. 22, 2003.

(51) Int. Cl.
*A61F 2/42* (2006.01)

(52) U.S. Cl.
USPC .................................................. 623/21.11

(58) Field of Classification Search
USPC .......... 623/21.11–21.17, 19.11–19.14, 16.11, 623/18.11, 20.22
See application file for complete search history.

(56) References Cited

U.S. PATENT DOCUMENTS

| | | | | |
|---|---|---|---|---|
| 3,506,982 A | * | 4/1970 | Steffee | 623/21.16 |
| 3,593,342 A | * | 7/1971 | Niebauer et al. | 623/23.41 |
| 3,745,590 A | * | 7/1973 | Stubstad | 623/13.11 |
| 3,837,008 A | * | 9/1974 | Bahler et al. | 623/21.13 |
| 3,909,853 A | * | 10/1975 | Lennox | 623/21.13 |
| 4,003,096 A | * | 1/1977 | Frey | 623/21.13 |

(Continued)

FOREIGN PATENT DOCUMENTS

| | | |
|---|---|---|
| DE | 25900476 U1 | 9/1995 |
| DE | 10237016 A1 | 2/2004 |

(Continued)

OTHER PUBLICATIONS

Hatano et al., "A ceramic prosthesis for the treatment of tumours of the distal radius," The Journal of Bone and Joint Surgery (Br), Dec. 2006, vol. 88-B, No. 12, pp. 1656-1659.

(Continued)

*Primary Examiner* — Alvin Stewart
(74) *Attorney, Agent, or Firm* — Morgan, Lewis & Bockius LLP

(57) ABSTRACT

A wrist implant requires minimal resection of the distal radius and preserves the sigmoid notch and articulation with the head of the distal ulna. The wrist implant generally includes a radius portion, a carpal portion and a carpal ball. The wrist implant includes a primary articulation and a secondary rotational articulation. The primary articulation occurs between the radius portion and the carpal ball. The secondary articulation occurs between the carpal ball and the carpal portion.

17 Claims, 12 Drawing Sheets

(56) References Cited

U.S. PATENT DOCUMENTS

| | | | |
|---|---|---|---|
| 4,040,130 A * | 8/1977 | Laure | 623/21.13 |
| 4,063,314 A * | 12/1977 | Loda | 623/21.13 |
| 4,100,626 A * | 7/1978 | White | 623/21.12 |
| 4,106,128 A * | 8/1978 | Greenwald et al. | 623/21.13 |
| 4,178,640 A * | 12/1979 | Buechler et al. | 623/21.12 |
| 4,180,871 A * | 1/1980 | Hamas | 623/21.13 |
| 4,229,840 A | 10/1980 | Gristina | |
| 4,229,841 A | 10/1980 | Youm et al. | |
| 4,242,759 A * | 1/1981 | White | 623/21.15 |
| 4,259,752 A * | 4/1981 | Taleisnik | 623/21.13 |
| 4,307,473 A * | 12/1981 | Weber | 623/21.12 |
| 4,645,505 A * | 2/1987 | Swanson | 623/21.12 |
| 4,714,476 A * | 12/1987 | Ranawat et al. | 623/21.12 |
| 4,784,661 A | 11/1988 | Beckenbaugh | |
| 4,936,854 A * | 6/1990 | Swanson | 623/21.12 |
| 5,080,673 A * | 1/1992 | Burkhead et al. | 623/19.11 |
| 5,108,444 A * | 4/1992 | Branemark | 623/21.12 |
| 5,314,485 A * | 5/1994 | Judet | 623/21.13 |
| 5,326,364 A * | 7/1994 | Clift et al. | 623/21.11 |
| 5,413,609 A * | 5/1995 | Nicol et al. | 623/21.15 |
| 5,458,646 A * | 10/1995 | Giachino et al. | 623/21.12 |
| 5,507,821 A * | 4/1996 | Sennwald et al. | 623/21.13 |
| 5,522,900 A * | 6/1996 | Hollister | 128/898 |
| 5,549,690 A * | 8/1996 | Hollister et al. | 623/21.15 |
| 5,593,448 A * | 1/1997 | Dong | 623/19.11 |
| 5,702,447 A * | 12/1997 | Walch et al. | 623/19.11 |
| 5,702,470 A * | 12/1997 | Menon | 623/21.12 |
| 5,741,335 A | 4/1998 | Gerber | |
| 5,766,258 A * | 6/1998 | Simmen | 623/21.12 |
| 5,782,926 A | 7/1998 | Lamprecht | |
| 5,800,551 A | 9/1998 | Williamson | |
| 5,824,106 A * | 10/1998 | Fournol | 623/21.18 |
| 5,853,413 A | 12/1998 | Carter | |
| 6,051,751 A * | 4/2000 | Sioshansi et al. | 128/898 |
| 6,059,832 A * | 5/2000 | Menon | 623/21.15 |
| 6,126,690 A * | 10/2000 | Ateshian et al. | 623/22.4 |
| 6,159,247 A * | 12/2000 | Klawitter et al. | 623/21.15 |
| 6,168,630 B1 * | 1/2001 | Keller et al. | 623/21.11 |
| 6,221,073 B1 | 4/2001 | Weiss | |
| 6,228,119 B1 * | 5/2001 | Ondrla et al. | 623/19.11 |
| 6,352,560 B1 * | 3/2002 | Poeschmann et al. | 623/23.4 |
| 6,454,808 B1 * | 9/2002 | Masada | 623/21.15 |
| 6,485,520 B1 * | 11/2002 | Hubach et al. | 623/21.13 |
| 6,514,287 B2 * | 2/2003 | Ondrla et al. | 623/19.13 |
| RE38,409 E | 1/2004 | Noiles | |
| 6,679,916 B1 * | 1/2004 | Frankle et al. | 623/19.12 |
| 6,746,486 B1 * | 6/2004 | Shultz et al. | 623/21.12 |
| 6,790,228 B2 | 9/2004 | Hossainy | |
| 6,790,234 B1 * | 9/2004 | Frankle | 623/19.12 |
| 6,814,757 B2 * | 11/2004 | Kopylov et al. | 623/21.11 |
| 6,827,741 B2 | 12/2004 | Reeder | |
| 6,860,902 B2 * | 3/2005 | Reiley | 623/21.18 |
| 6,887,277 B2 * | 5/2005 | Rauscher et al. | 623/19.13 |
| 6,890,358 B2 * | 5/2005 | Ball et al. | 623/21.13 |
| 6,969,407 B2 * | 11/2005 | Klotz et al. | 623/21.12 |
| 6,986,790 B2 | 1/2006 | Ball | |
| 7,160,329 B2 * | 1/2007 | Cooney et al. | 623/20.11 |
| 7,160,331 B2 * | 1/2007 | Cooney et al. | 623/21.11 |
| 7,169,184 B2 * | 1/2007 | Dalla Pria | 623/19.12 |
| 7,241,314 B1 | 7/2007 | Winslow | |
| 7,531,003 B2 * | 5/2009 | Reindel | 623/21.12 |
| 7,608,109 B2 * | 10/2009 | Dalla Pria | 623/19.11 |
| 7,625,408 B2 * | 12/2009 | Gupta et al. | 623/21.11 |
| 7,628,819 B2 * | 12/2009 | Gupta et al. | 623/21.11 |
| 7,708,781 B2 * | 5/2010 | Scheker | 623/20.11 |
| 7,766,970 B2 * | 8/2010 | Shultz et al. | 623/21.14 |
| 7,914,583 B2 | 3/2011 | Wolfe | |
| 7,918,894 B2 * | 4/2011 | Wolfe et al. | 623/21.14 |
| 8,052,757 B1 * | 11/2011 | Scheker | 623/21.13 |
| 8,070,820 B2 * | 12/2011 | Winslow et al. | 623/19.13 |
| 8,118,876 B2 * | 2/2012 | Gupta et al. | 623/21.11 |
| 8,152,854 B2 * | 4/2012 | Imbriglia et al. | 623/21.12 |
| 8,333,806 B2 * | 12/2012 | Scheker | 623/21.13 |
| 2001/0011192 A1 * | 8/2001 | Ondrla et al. | 623/19.13 |
| 2001/0025199 A1 * | 9/2001 | Rauscher | 623/21.13 |
| 2002/0055785 A1 * | 5/2002 | Harris | 623/21.11 |
| 2002/0082705 A1 * | 6/2002 | Bouman et al. | 623/21.11 |
| 2003/0135280 A1 * | 7/2003 | Kopylov et al. | 623/21.12 |
| 2003/0187511 A1 * | 10/2003 | Ball et al. | 623/21.13 |
| 2003/0216813 A1 * | 11/2003 | Ball et al. | 623/21.12 |
| 2004/0117025 A1 * | 6/2004 | Reindel | 623/18.11 |
| 2004/0138756 A1 * | 7/2004 | Reeder | 623/21.11 |
| 2004/0220673 A1 * | 11/2004 | Pria | 623/19.12 |
| 2004/0220674 A1 * | 11/2004 | Pria | 623/19.12 |
| 2004/0220678 A1 * | 11/2004 | Chow et al. | 623/21.11 |
| 2004/0230312 A1 * | 11/2004 | Hanson et al. | 623/21.12 |
| 2005/0004675 A1 * | 1/2005 | Shultz et al. | 623/21.14 |
| 2005/0049710 A1 * | 3/2005 | O'Driscoll et al. | 623/20.11 |
| 2005/0085921 A1 * | 4/2005 | Gupta et al. | 623/21.13 |
| 2005/0171613 A1 * | 8/2005 | Sartorius et al. | 623/21.13 |
| 2006/0004462 A1 * | 1/2006 | Gupta | 623/21.13 |
| 2006/0030946 A1 * | 2/2006 | Ball et al. | 623/21.13 |
| 2006/0036330 A1 | 2/2006 | Shultz et al. | |
| 2006/0052725 A1 * | 3/2006 | Santilli | 600/587 |
| 2006/0069446 A1 * | 3/2006 | Ragusa et al. | 623/21.11 |
| 2006/0161260 A1 | 7/2006 | Thomas | |
| 2006/0200248 A1 * | 9/2006 | Beguin et al. | 623/19.11 |
| 2007/0055381 A1 | 3/2007 | Berelsman et al. | |
| 2007/0073409 A1 | 3/2007 | Cooney, III | |
| 2007/0100458 A1 * | 5/2007 | Dalla Pria | 623/19.13 |
| 2007/0142919 A1 | 6/2007 | Cooney, III | |
| 2007/0185582 A1 | 8/2007 | Palmer | |
| 2007/0185584 A1 | 8/2007 | Kaufmann | |
| 2007/0198095 A1 | 8/2007 | VanDer Meulen et al. | |
| 2007/0225820 A1 | 9/2007 | Thomas | |
| 2007/0244563 A1 * | 10/2007 | Roche et al. | 623/19.12 |
| 2008/0027558 A1 | 1/2008 | Palmer et al. | |
| 2008/0051909 A1 | 2/2008 | Wolfe | |
| 2009/0149961 A1 * | 6/2009 | Dallmann | 623/19.11 |
| 2009/0164021 A1 * | 6/2009 | Dallmann | 623/19.11 |
| 2009/0198244 A1 | 8/2009 | Leibel | |
| 2009/0254189 A1 * | 10/2009 | Scheker | 623/21.11 |
| 2010/0010636 A1 * | 1/2010 | Shultz et al. | 623/21.12 |
| 2010/0185295 A1 * | 7/2010 | Emmanuel | 623/21.11 |
| 2010/0222886 A1 * | 9/2010 | Wiley et al. | 623/19.13 |
| 2011/0066250 A1 * | 3/2011 | Palmer | 623/21.12 |
| 2012/0078376 A1 * | 3/2012 | Vanasse et al. | 623/21.12 |
| 2012/0136453 A1 * | 5/2012 | Scheker et al. | 623/21.12 |
| 2012/0259418 A1 * | 10/2012 | Cooney et al. | 623/21.12 |
| 2012/0277880 A1 * | 11/2012 | Winslow et al. | 623/19.11 |

FOREIGN PATENT DOCUMENTS

| | | |
|---|---|---|
| EP | 0034192 A1 | 8/1981 |
| EP | 0607749 A1 | 7/1994 |
| EP | 1062924 A1 | 12/2000 |
| EP | 1066807 A1 | 1/2001 |
| EP | 1437104 A1 | 7/2004 |
| FR | 2669214 A1 | 5/1992 |
| FR | 2673100 A1 | 8/1992 |
| FR | 2728283 A1 | 7/1996 |
| FR | 2805151 A1 | 8/2001 |
| FR | 2833480 A1 | 6/2003 |
| FR | 2875127 A1 | 3/2006 |
| GB | 1412376 | 11/1975 |
| GB | 2269752 A | 2/1994 |
| GB | 2308068 A | 6/1997 |
| GB | 2392097 A | 2/2004 |
| JP | 7241306 | 9/1995 |
| JP | 11332893 | 12/1999 |
| WO | 97/10780 A1 | 3/1997 |
| WO | 2004/026169 A2 | 4/2004 |
| WO | 2006/136940 A2 | 12/2006 |

OTHER PUBLICATIONS

Lawler et al., "Total Wrist Arthroplasty," Bulletin of the NYU Hospital for Joint Diseases, 2006, vol. 64, Nos. 3 and 4, pp. 98-105.

Takwale et al., "Biaxial total wrist replacement in patients with rheumatoid arthritis," The Journal of Bone and Joint Surgery (Br), Jul. 2002, vol. 84-B, No. 5, pp. 692-699.

Tolbert et al., "The Kinetics of Normal and Prosthetic Wrists," J. Biomechanics, 1985, vol. 18, No. 12, pp. 887-897.

(56) References Cited

OTHER PUBLICATIONS

Youm et al., "Design of a Total Wrist Prosthesis," Annals of Biomedical Engineering, 1984, vol. 12, pp. 247-262.

Swanson et al., "Flexible Implant Arthroplasty of the Radiocarpal Joint," Clinical Orthopedics and Related Research, ' Jul./Aug. 1984, No. 187, pp. 94-106.

Beckenbaugh, "Implant arthroplasty in the rheumatoid hand and wrist: Current state of the art in the United States," The Journal of Hand Surgery, Sep. 1983, vol. 8, No. 5, Part 2, pp. 675-678.

Levadoux et al., "Total Wrist Arthroplasty with Destot Prostheses in Patients with Posttraumatic Arthritis," The Journal of Hand Surgery, May 2003, vol. 28A, No. 3, pp. 405-413.

Boyer et al., "Distal Radius Hemiarthroplasty Combined with Proximal Row Carpectomy: Case Report," The Iowa Orthopaedic Journal, 2010, vol. 30, pp. 168-173.

Gokaraju et al., "Use of a Distal Radius Endoprosthesis Following Resection of a Bone Tumour: A Case Report," Sarcoma, 2009, vol. 2009, Article ID 938295.

U.S. Appl. No. 60/411,824, filed Sep. 18, 2002, by Reindel.

\* cited by examiner

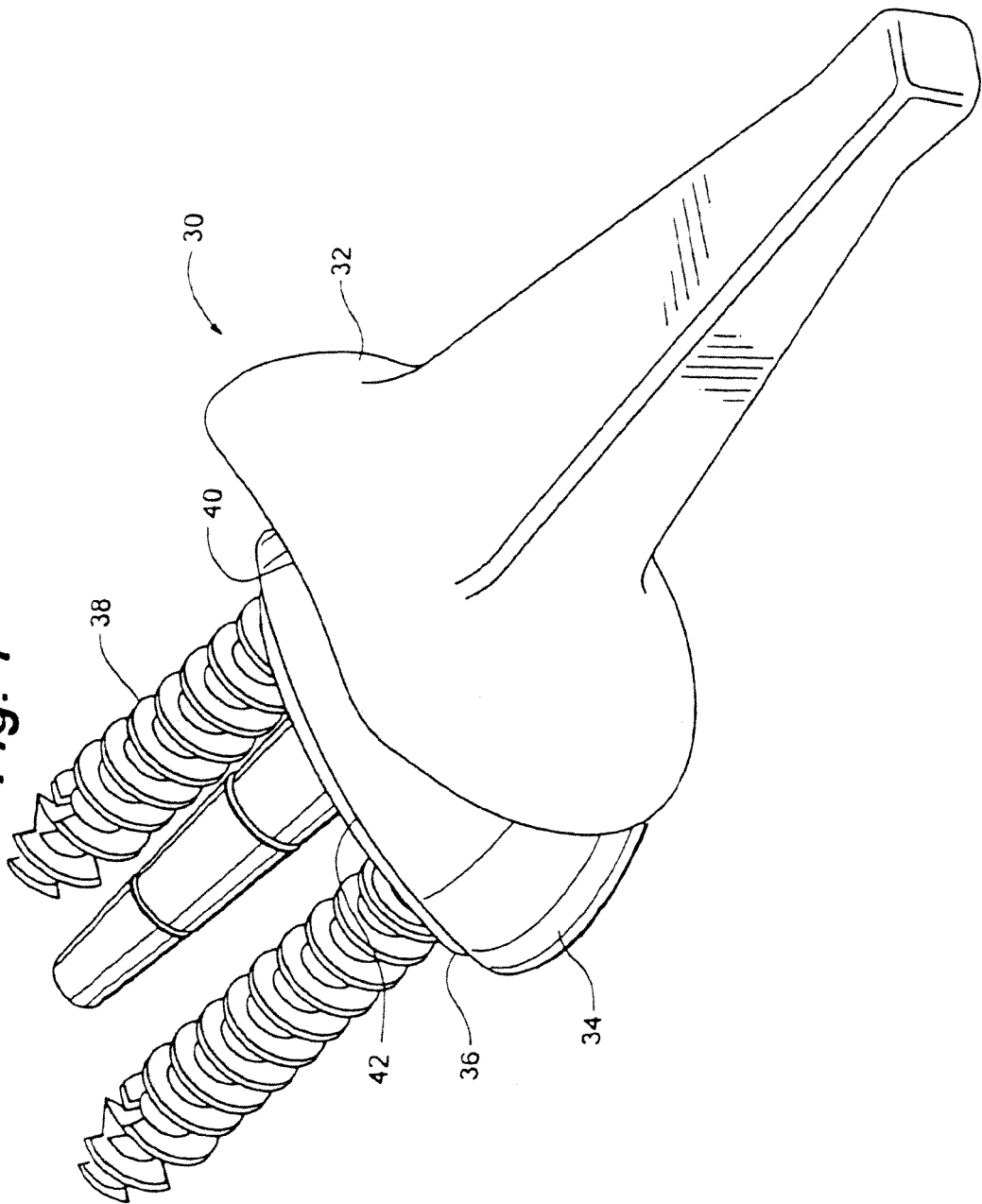

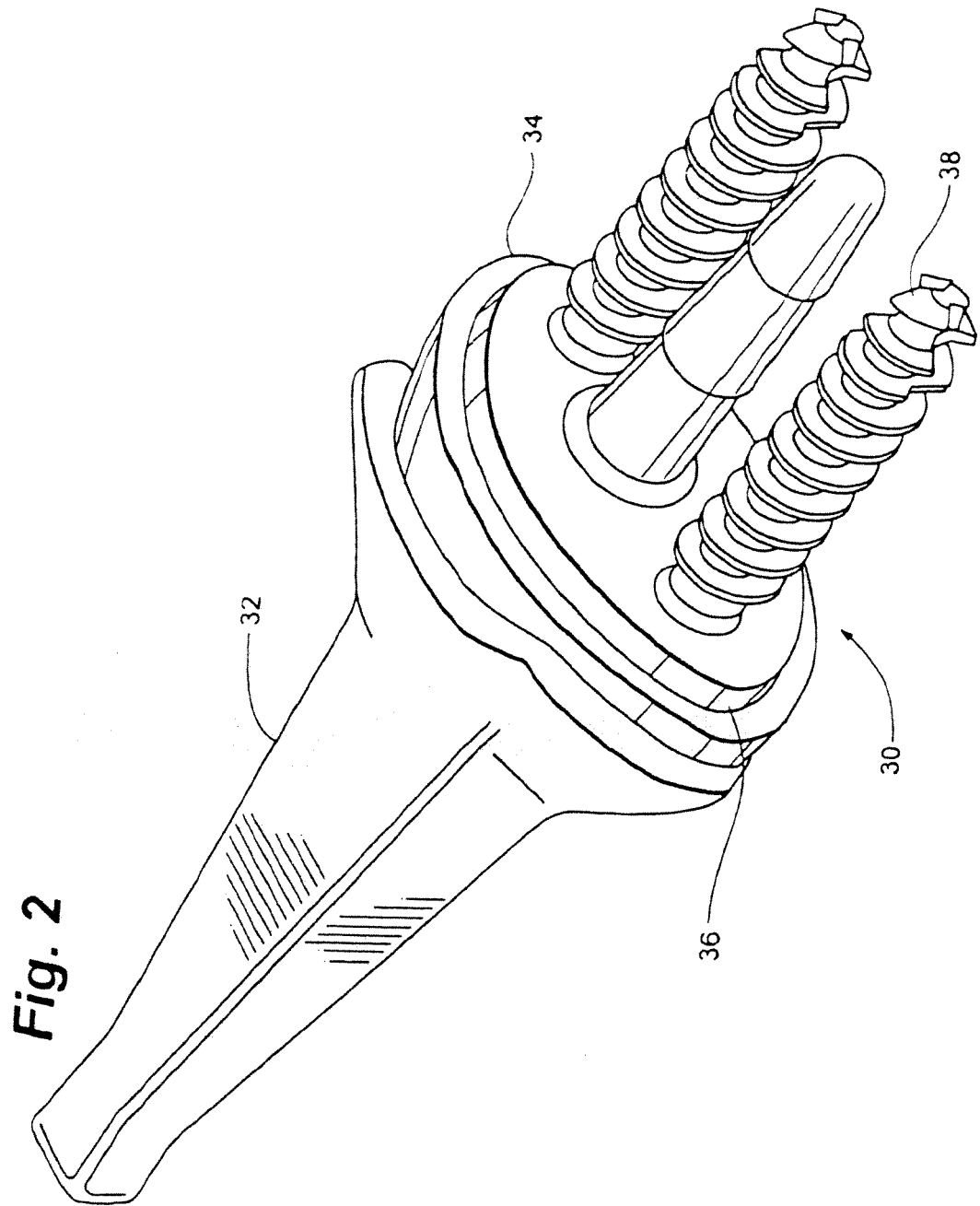

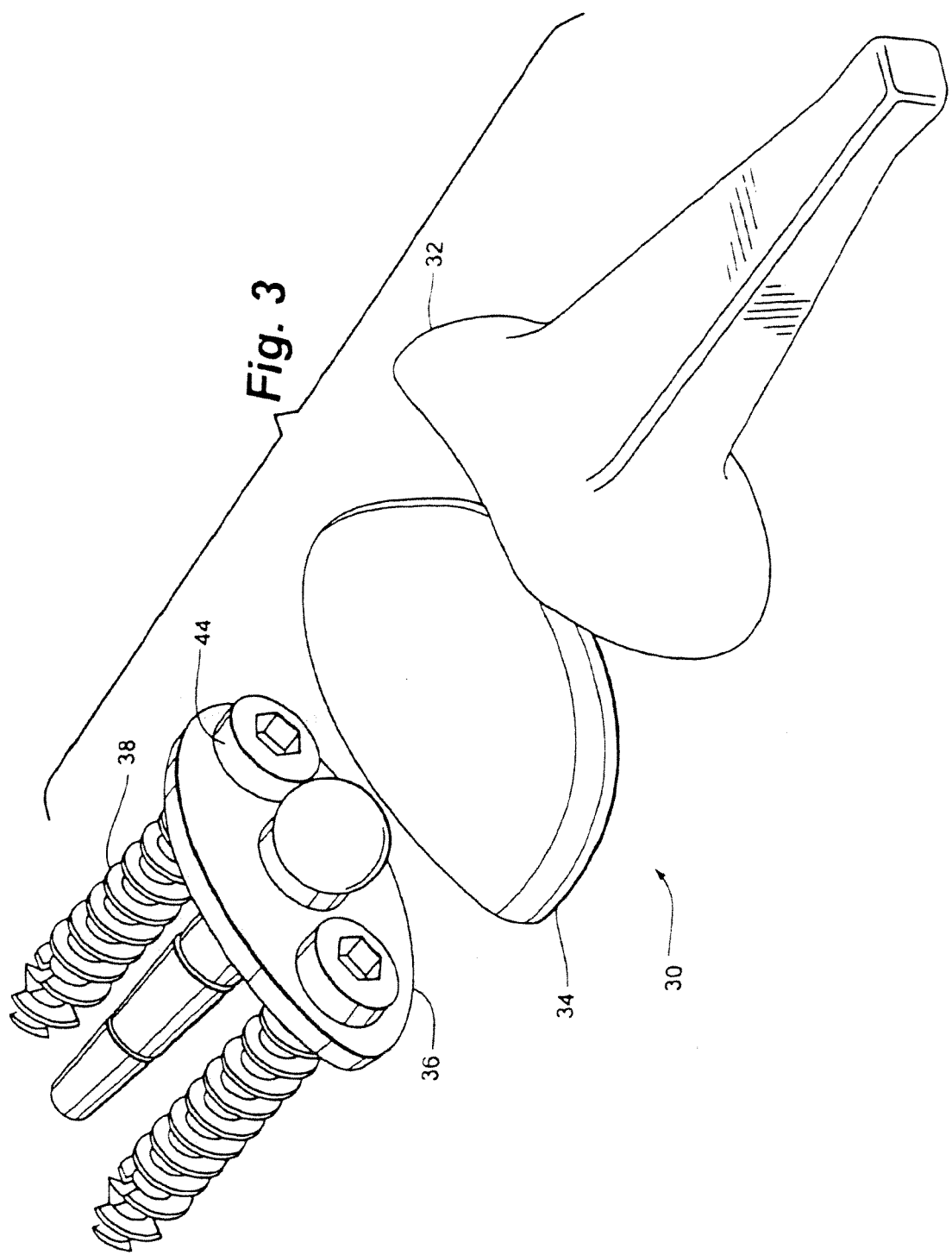

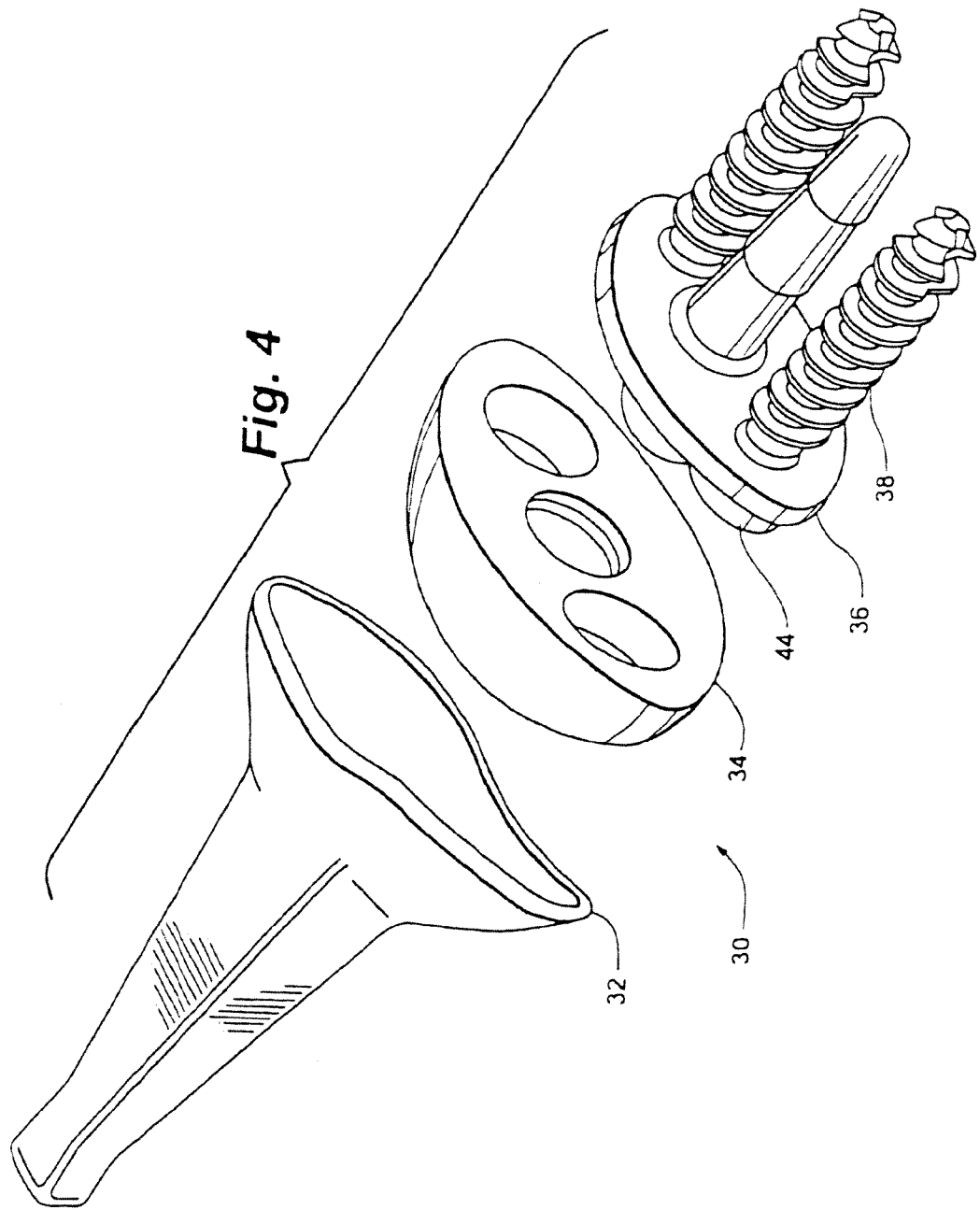

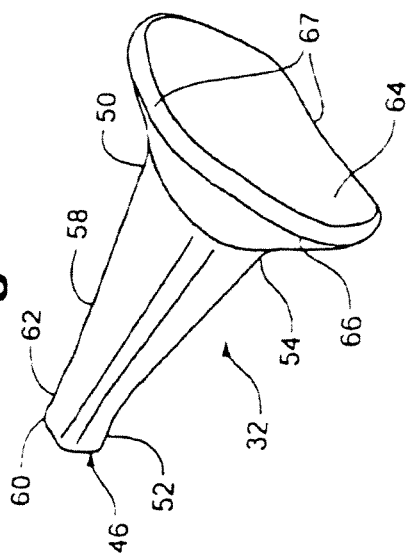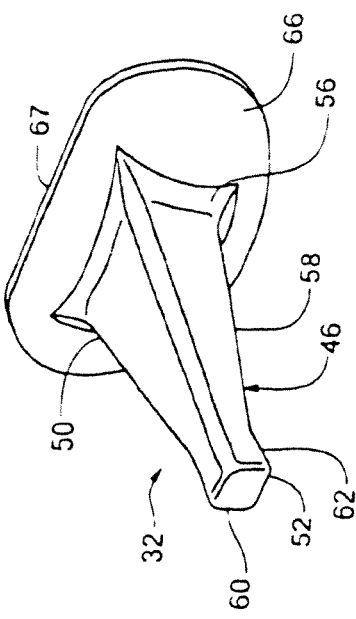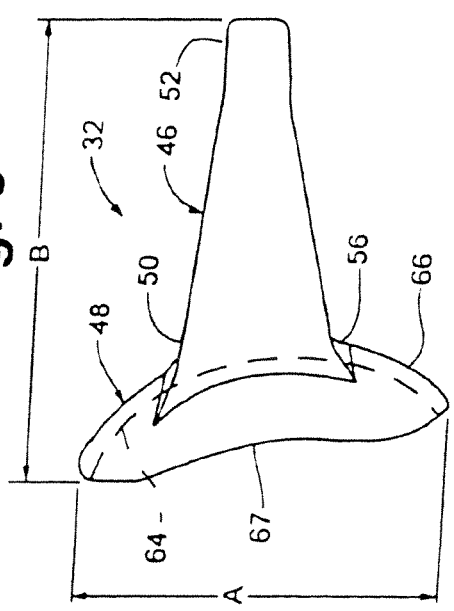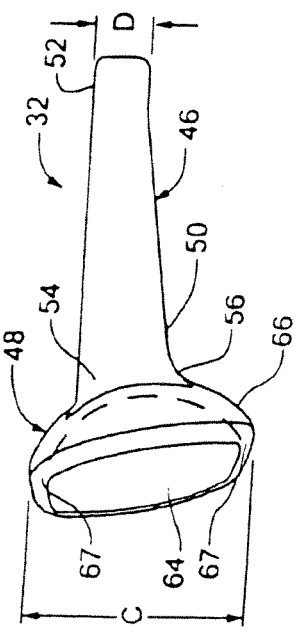

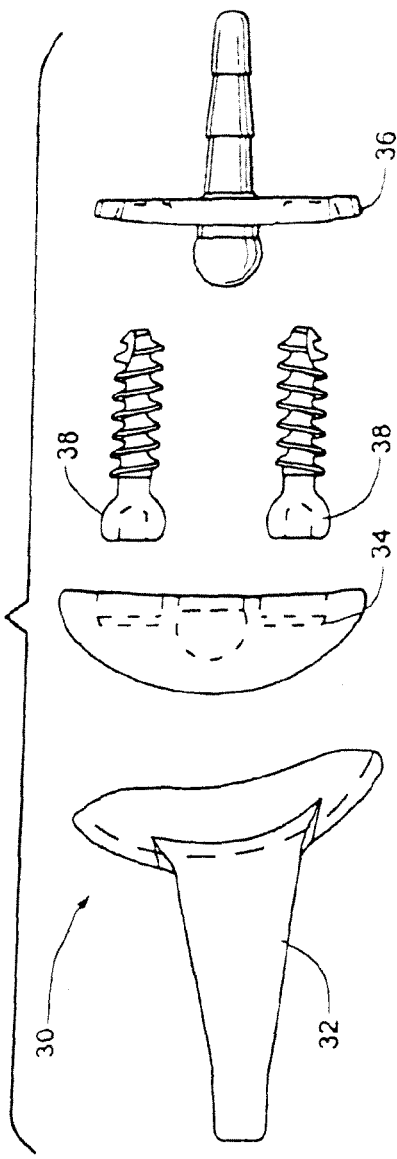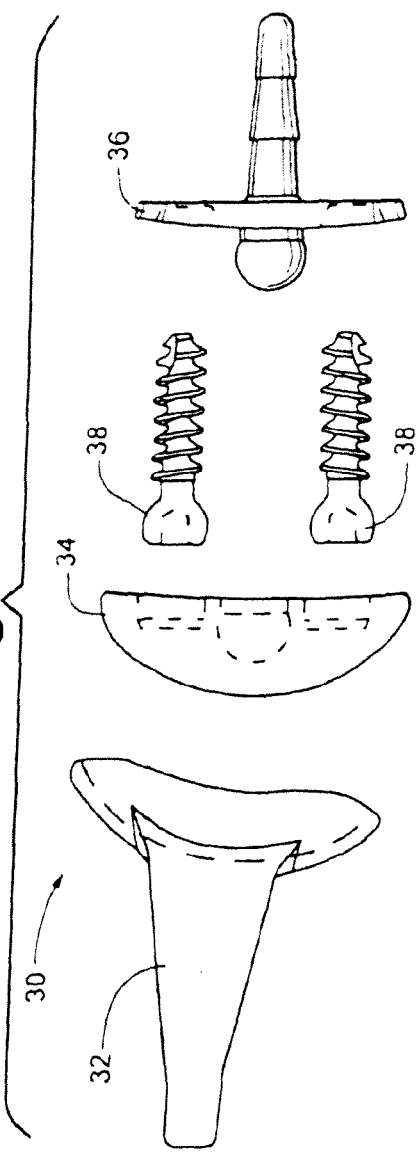

PROSTHETIC WRIST IMPLANT

CROSS REFERENCE TO RELATED APPLICATIONS

This application is a continuation of U.S. patent application Ser. No. 12/626,578, filed Nov. 25, 2009, which is a continuation of U.S. patent application Ser. No. 11/210,416, filed Aug. 24, 2005, now U.S. Pat. No. 7,628,819, which is a divisional of U.S. patent application Ser. No. 10/897,317, filed Jul. 22, 2004, now U.S. Pat. No. 7,625,408, which claims the benefit of U.S. Provisional Patent Application No. 60/489,037, filed Jul. 22, 2003, each of which is incorporated herein by reference in its entirety.

FIELD OF THE INVENTION

The invention relates to prosthetic orthopedic implants. More particularly the invention relates to a prosthetic orthopedic wrist implant for prosthetic replacement of a damaged, diseased or degenerated natural wrist joint.

BACKGROUND

Orthopedic replacement of damaged or degenerated natural wrist joints is well known in the orthopedic arts. Prior to the introduction of prosthetic joint replacement for the wrist, individuals suffering from a joint disease in the wrist such as radio-carpal arthritis were often surgically treated by a fusion procedure. Fusion involves repairing the injured wrist joint structures with a fixed plate or rod that stiffens the wrist. That is, the joint is fixed in position by a device that allows no movement of the wrist. While this was an improvement over a diseased or injured wrist joint it is clearly unsatisfactory.

Existing orthopedic prostheses for wrist joint implantation have a number of limitations. Currently, most prosthetic wrist implants provide the patient with only limited functionality of the wrist, otherwise the implant becomes unstable. The natural wrist is astonishingly flexible in its freedom of motion. If a prosthetic wrist implant does not provide sufficient motion in flexion, extension, radial deviation, or ulnar deviation, the patient may have difficulty performing many of the normal tasks of daily living. Ideally, after implantation of a wrist prosthesis, the wrist will have a range of motion equal to or at least approaching that of a natural wrist joint.

An important requirement for prosthetic wrist implants is to have an extremely secure attachment between the implant and the bones. Separation of the prosthetic wrist implant from the bones to which it has been secured can be a serious complication requiring a repeat surgical procedure to make repairs. Failure of the attachment between the wrist prosthesis and the bones to which it is attached will cause further damage to the bones in some circumstances, making it difficult or impossible to treat the wrist even with a replacement implant. Prosthetic wrist implants currently in use generally require resection of the peripheral rim of the distal radius with its important ligaments and soft tissue attachments. The loss of these ligamentous attachments tends to create instability (looseness) of the prosthetic wrist. To compensate for this instability, a more involved surgical procedure must be performed to make reattachments of the soft tissue to the bone.

In addition, some currently available prosthetic wrist implants require the resection of a substantial amount of bone from the carpal bone structures. This substantial resection relocates the normal wrist centers of rotation (or motion) and relocation of the centers of wrist rotation interferes with normal function of the wrist extensor and flexor tendons, alters tendon moment arms and, as a result, limits and weakens movement of the wrist in extension and flexion. Further, if a patient later needs another procedure at the same joint revision options are limited if excessive tissue has been resected.

Another shortcoming of existing prosthetic wrist implants is the limitation of torsional movement of the wrist related the elbow. The healthy hand and wrist are able to rotate about an axis generally parallel to that of the long axis of the forearm, both because of the rotation of the radius and the ulna about one another, and because of the rotation of the natural wrist bones with relation to the radius and the ulna. Currently available prosthetic wrist implants typically involve the secure attachment of a proximal component of the wrist implant to the distal end of the radius and a distal component to the carpus with fixed planes of motion that result in a loss of torsional range of motion. In addition, if the forces involved in torsional movement of the wrist are limited by the implant as with current designs, those forces are transferred to the bone-implant interfaces at the radius and the carpus, increasing the risk of the implant loosening, and contributing to implant failure.

Further, in some wrist implant designs, a single stem extends through the carpus and into one or more of the metacarpals. The distal component of these wrist implants tends to erode through the metacarpal bone and create instability of the carpal attachment. Consequently the distal component of the implant may loosen or fracture where the implant enters the bones of the hand. In addition, in the normal wrist there is some freedom of motion between the carpals and the metacarpals and a stem passing through the carpals and into the metacarpals limits that freedom of motion resulting in less than ideal function of the wrist after implantation.

In addition, it has been found that implants that allow metal to metal contact between the radial and carpal components tend to cause shedding of metal particles that may migrate into surrounding tissues and may cause tissue necrosis and consequent implant failure and other complications.

Thus, it would be valuable to provide an improved orthopedic wrist implant that would provide a range of motion simulating the natural wrist's range of motion as closely as possible. In addition, it would be desirable if a prosthetic wrist implant would provide an improved torsional range of motion and reduce the effect of torsional forces on the bone-implant interface. It would further be desirable that a prosthetic wrist implant provide a secure, strong, and stable attachment to the surrounding bones in order to provide a wrist implant that would have low complications related to implant loosening. Further, it would be beneficial to preserve the peripheral rim of distal radius as well as the sigmoid notch of the distal radius where it articulates with the head of the ulna. It would be preferable to avoid metal-to-metal contact between the radial and carpal components.

SUMMARY OF THE INVENTION

The prosthetic wrist implant of the present invention solves many of the above limitations and problems related to wrist implant failure. The wrist implant of the present invention requires little or no resection of the distal radius and minimal resection of the carpal bones of the wrist. The implant is available in left and right hand configurations with geometrically scaled sizes that approximate the anthropomorphic sizes of different radio-carpal joints. The wrist implant generally includes a radius portion, a carpal portion and a carpal ball. The radial component of the prosthetic wrist implant is designed much like a surface replacement arthroplasty (SRA) in that it seats against the scaphoid and lunate fossae and preserves the peripheral rim of the distal radius with its important ligamentous and soft tissue attachments. This configuration requires minimal or no resection of the distal radius and preserves the sigmoid notch and articulation of the distal radius with the head of the distal ulna.

The carpal portion of the wrist implant is a low-profile design that minimizes the amount of bone resection and does not interfere with the normal function of the wrist extensor and flexor tendons. The carpal portion of the wrist implant may include a central stem for insertion into the capitate bone. The carpal portion accommodates two carpal screws for fixation to the scaphoid and hamate bones within the distal carpal row.

A carpal ball component preferably acts as an intercalated segment that articulates with both the radius and carpal portions of the implant. The primary articulation occurs with the radial component. The primary articulating surfaces may be ellipsoidal and toroidal and act along two perpendicular axes of rotation. The first axis lies in the coronal plane and the second axis lies in the sagittal plane thus permitting motion in flexion-extension and radial-ulnar deviation. The concavity of the radial portions' articular geometry resists ulno-volarly directed forces that can cause excessive wear and implant subluxation or dislocation.

In one embodiment a secondary articulation of the carpal ball component occurs with a carpal plate. This articulation is rotational and occurs about an axis aligned generally parallel with the longitudinal axis of the third metacarpal bone. This additional degree of freedom diverts torsional forces from the bone implant interfaces, thus reducing the risk of implant loosening and lessening the risk of implant failure. This additional degree of freedom of movement also compensates for potential misalignment of the implant due to advanced deformity of the injured wrist caused, for example, by rheumatoid or degenerative arthritis.

The interface between the ellipsoidal carpal ball and the toroidal radial component allows flexion-extension and radio-ulnar motion to occur about different axes of rotation. This allows for a hinge like motion dorso-palmarly and a gliding motion radio-ulnarly closely approximating natural joint kinematics.

BRIEF DESCRIPTION OF THE DRAWINGS

FIG. 1 is a perspective view of a prosthetic wrist implant in accordance with the present invention;

FIG. 2 is a perspective view of the prosthetic wrist implant from a reverse angle to that of FIG. 1;

FIG. 3 is an exploded view of the prosthetic wrist implant;

FIG. 4 is a exploded perspective view of the prosthetic wrist implant from a reverse angle to that of FIG. 3;

FIG. 5 is a plan view of a radius component in accordance with the present invention;

FIG. 6 is an elevational view of the radius component in accordance with the present invention;

FIG. 7 is a perspective view of the radius component;

FIG. 8 is a second perspective view of the radius component;

FIGS. 20a and 20b are exploded plan views showing the right and left hand configurations of the prosthetic wrist implant;

DETAILED DESCRIPTION OF THE DRAWINGS

Figure 21:
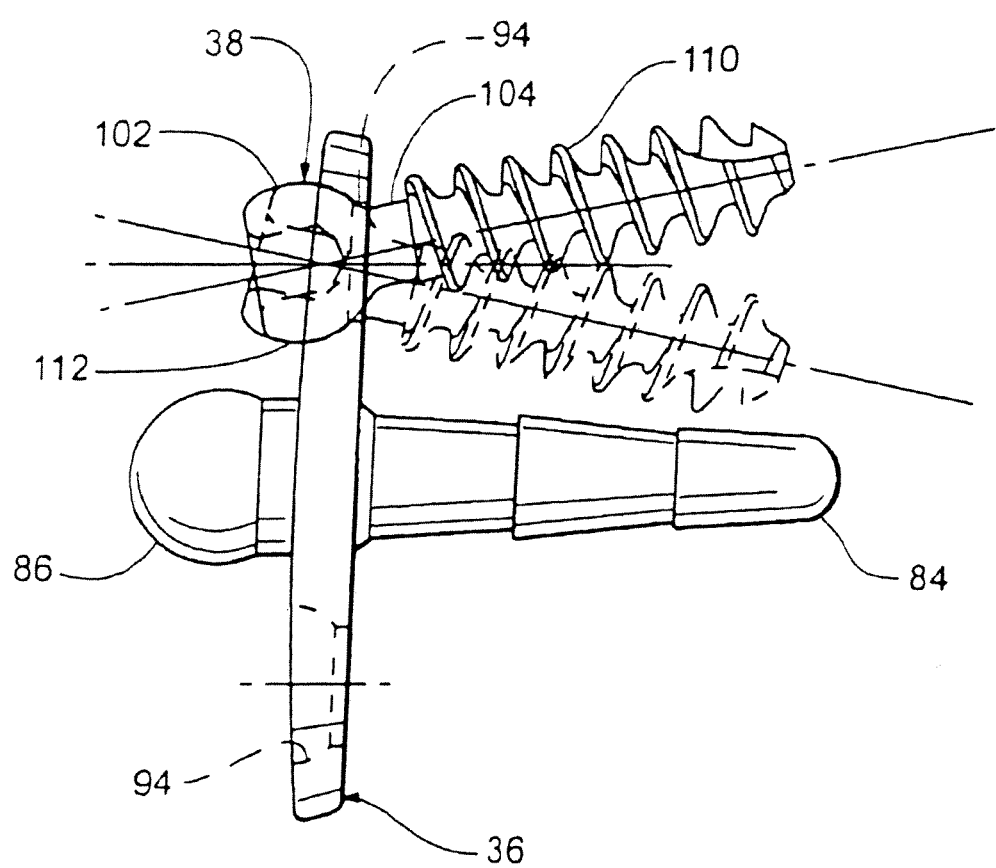
FIG. 21 is a plan view showing the articulation of one embodiment of a carpal plate and carpal screw in accordance with the present invention.
Figure 22:
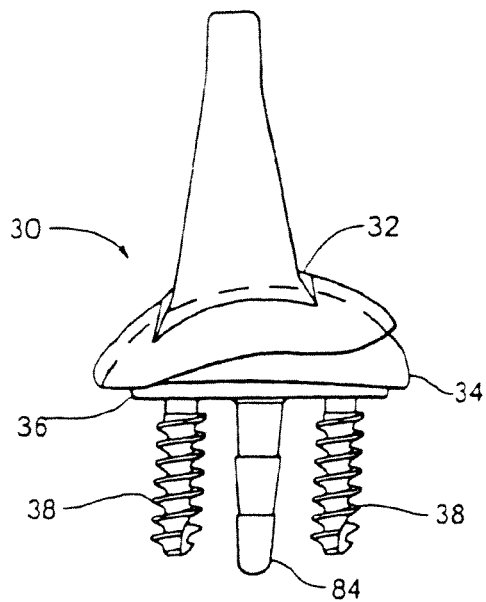
FIG. 22 is a plan view of the articulated parts of a prosthetic wrist implant.
Figure 23:
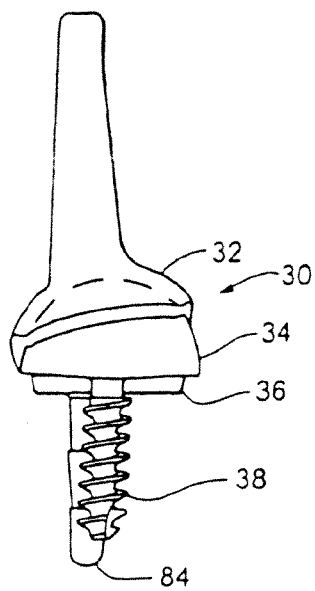
FIG. 23 is an elevational view of the articulated parts of the prosthetic wrist implant.
Figure 24:
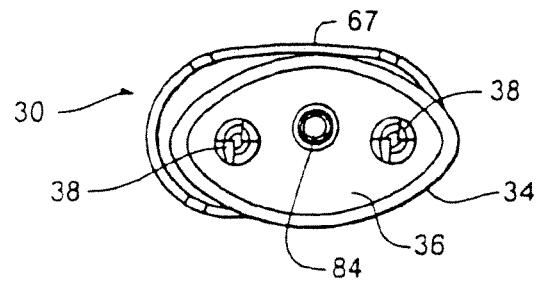
FIG. 24 is an end view of the articulated parts of the prosthetic wrist implant.
Figure 25A:
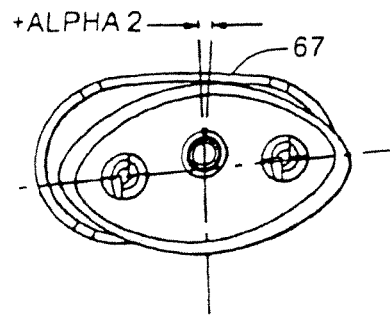
FIGS. 25a and 25b depict the tertiary articulation of the carpal plate and carpal ball in accordance with one embodiment of the present invention.
Figure 25B:
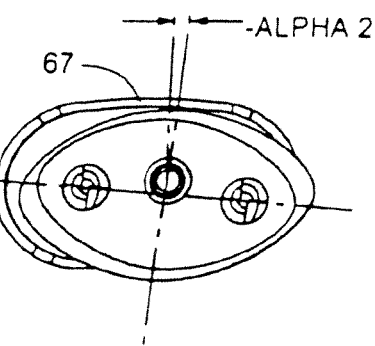
Figure 26A:
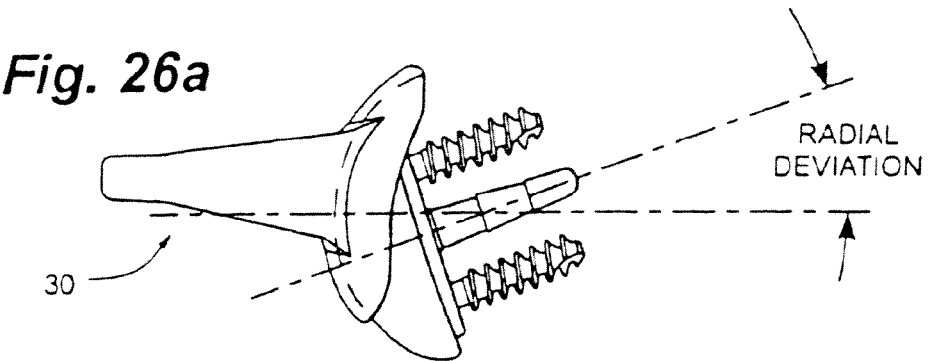
FIGS. 26a-d depict the radial deviation, extension, ulnar deviation, and flexion of the primary articulation of an embodiment of the present invention.
Figure 26B:
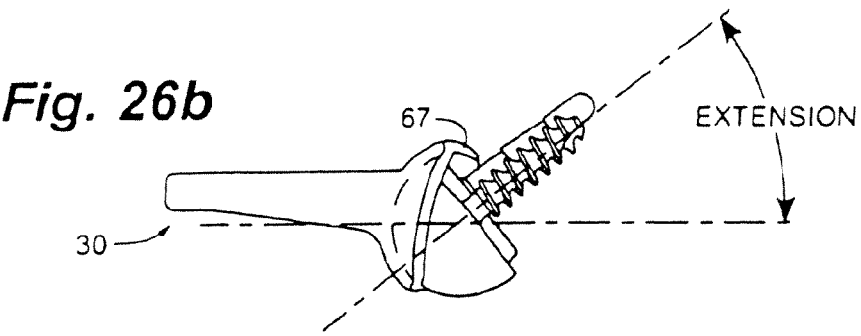
Figure 26C:
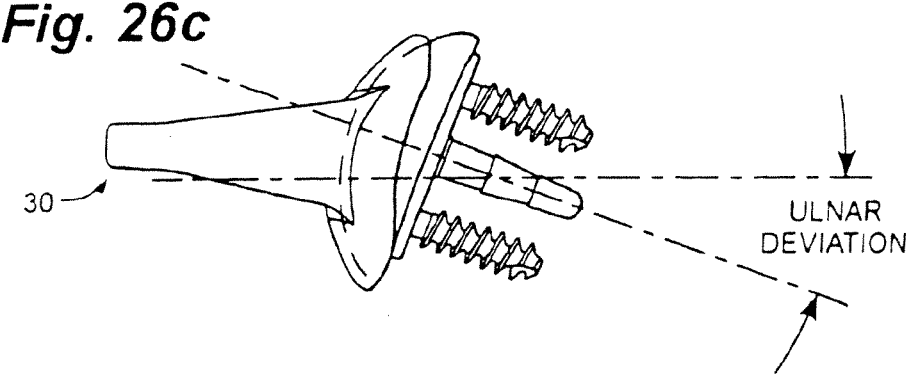
Figure 26D:
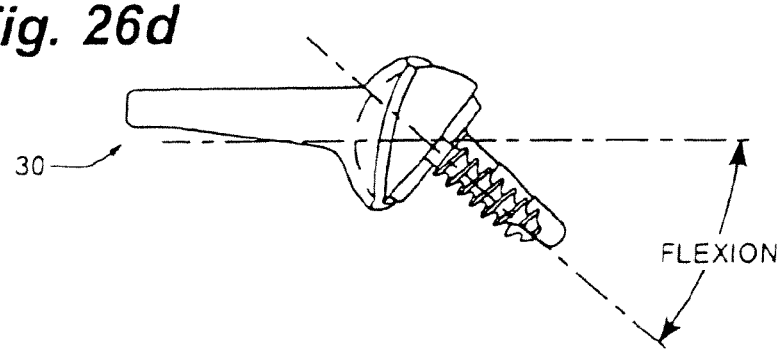

A wrist implant 30 of the present invention generally includes radius component 32, carpal ball 34, carpal plate 36 and one or more carpal screws 38. Referring to FIGS. 1-4 radius component 32 articulates with carpal ball 34 via a primary articulation 40. Carpal ball 34 articulates with carpal plate 36 via secondary articulation 42 as best seen in FIG. 25. Carpal screws 38 articulate with carpal plate 36 via tertiary articulation 44, as best seen in FIG. 21.

Referring, in particular, to FIGS. 5-8, radius component 32 generally includes intra-medullary stem 46 and articular cup 48. In one embodiment, intra-medullary stem 46 is generally quadrilateral in cross-section and tapers from broad at a first end 5C to narrower at second end 52. Preferably, intra-medullary stem 46 and articular cup 48 are formed, cast or machined as an integral unit from a single piece of material. The juncture 54 between intra-medullary stem 46 and articular cup 48 is tapered in a fillet 56. Each corner 58 of intra-medullary stem 46 is radiused, beveled or chamfered. Intra-medullary stem 46 further defines rounded end 60 and a straight portion 62. Intra-medullary stem 46 also defines a stem thickness D. Intra-medullary stem 46 has a smooth continuous surface throughout and may be surface treated to encourage osseointegration. Thus, stem geometry emulates the intra-medullary contour of the distal radius. The smooth continuous surface of intra-medullary stem 46 means that medullary stem 46 lacks sharp corners or any significant discontinuities. The smooth continuous surface of intra-medullary stem 46 may include roughening of texture to encourage osseointegration while still retaining a smooth continuous shape.

Articular cup 48 is generally toroidal in shape and has a major dimension A and a minor dimension C. Articular cup 48 defines a generally toroidal concave articular surface 64. Articular surface 64 preferably has two perpendicular axes, one axis of rotation and one instantaneous center, which lie in generally coronal and sagittal planes. Articular surface 64 defines two radii, a major radius, R1 and a minor radius R2. Major radius R1 and minor radius R2 may be selected to emulate the curve traced by the proximal portion of the scaphoid-lunate complex in the normal articulation of the human wrist as is clearly seen in FIG. 26. Articular cup 48 further includes cup wall 66. Cup wall 66 is preferably of generally uniform thickness. Cup wall 66 is desirably curved to conform to the curvature of the scaphoid and lunate fossae of the distal end of the radius. Thus, the curvatures of articular surface 64 have generally shorter radii than does the exterior of cup wall 66. Articular cup 48 further defines dorsal and volar cutouts 67. The surface at dorsal and volar cutouts 67 is highly polished to facilitate the excursion of the flexor and extensor tendons and other soft tissues thereover. Dorsal and volar cutouts 67 also maximize range of motion in flexion and extension without metal to metal impingement of the radial and carpal components.

Articular surface 64 is, desirably, precision machined and highly polished for articulating with carpal ball 34. Radius component 32 is preferably fabricated from cobalt chrome-molybdenum alloy material. The juncture between intra-medullary stem 46 and articular cup 48 is angled to approximate the anatomical volar tilt and ulnar inclination angles of the distal radius. The articular surface 64 of the articular cup 48 is angled volarly and ulnarly. Ulnar inclination may be about twenty to twenty two degrees and volar tilt may be about ten to twelve degrees.

Intra-medullary stem 46 is offset in the anterior-posterior and lateral planes to align the articular cup 48 to seat against the lunate and scaphoid fossae and preserve the distal ulna. The intra-medullary stem 46 may be coated with a commercially pure titanium plasma coating to promote osseointegration.

Referring in particular to FIGS. 11, 12, 13 and 14, carpal ball 34 is generally ellipsoidal in shape. Carpal ball 34 has a convex articular surface 68. Convex articular surface 68 may be shaped to generally match articular surface 64 of articular cup 48 to provide a close sliding fit therewith. Carpal ball 34 defines slightly flattened but still rounded articular ends 70. Convex articular surface 68 has a major radius R1 and a minor radius R2 generally matching, respectively, those of articular cup 48. Carpal ball 34 also has a back surface 72. Back surface 72 is curved along a relatively flat secondary spherical radius SR1. Back surface 72 further defines socket 74, and, preferably, two oval excavations 76. Socket 74 includes rim 78 and spheroidal portion 80. Socket 74 is, desirably, generally spherical in shape having a rim 78 that is of a lesser diameter than spheroidal portion 80.

Carpal ball 34 has a major dimension B and a minor dimension D. Carpal ball 34 also presents a major curvature and a minor curvature.

Preferably, there are two oval excavations 76 on back surface 72. Oval excavations 76 are of an oval, ellipsoidal, arcuate or racetrack shape and of a generally uniform depth. Oval excavations 76 may be arcuate centered about socket 74.

Carpal ball 34 is made from ultra high molecular weight polyethylene (UHMWPE) or another self lubricating material. UHMWPE has the advantage of providing a thermal break as well as minimizing wear on the other articular components. However metals or other materials may also be utilized. Carpal ball 34 may be machined, molded or formed by other techniques known to the art.

In another embodiment of the invention, articular cup 48 defines a generally toroidal concave articular surface 64 that allows slight play between articular surface 64 and convex articular surface 68. In this embodiment, carpal ball 34 has a convex articular surface 68 that tapers slightly toward articular ends 70. Convex articular surface 68 is shaped to match articular surface 64 of articular cup 48 to provide a close sliding fit therewith near the center of convex articular surface 68 but a looser sliding fit near articular ends 70. It is important to note that the ellipsoidal geometry of the carpal ball 34 demonstrates a line-to-line contact of the carpal ball 34 and the articular Clip 48 in the anterior-posterior and lateral planes.

Referring in particular to FIGS. 15-19, carpal plate 36 generally includes plate 82, carpal stem 84 and ball 86.

Figure 17:
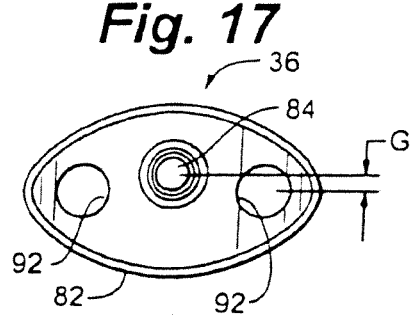
FIG. 17 is an end view of the carpal plate in accordance with the present invention.

Plate 82 includes buttress surface 88, secondary articular surface 90 and defines screw holes 92. Buttress surface 88 is preferably substantially flat. Secondary articular surface 90 is curved along spherical radius SR1 to match back surface 72 of carpal ball 34. This facilitates better wear characteristics between carpal ball 34 and carpal plate 36 by reducing peripheral stress risers that may cause fretting of the carpal ball 34 and, possibly, debris generation. Screw holes 92 pierce plate 82, preferably on opposite sides of ball 86. Screw holes 92 include spheroidal countersink 94 and cylindrical rim 95. Plate 82 is generally elliptical in shape as best seen in FIG. 17. The periphery of plate 82 is radiused at the edge of secondary articular surface 90. Distal to the radiused edge the periphery of plate 82 is drafted to optimize articular contact area and avoid metal to metal contact at the extremes of range of motion and axial rotation.

Figure 16:
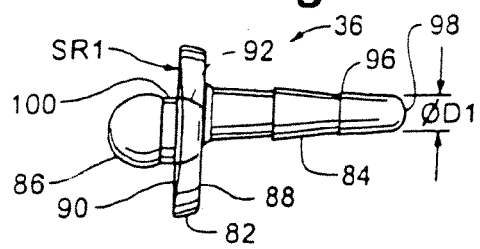
FIG. 16 is an elevational view of the carpal plate in accordance with the present invention.
Figure 19:
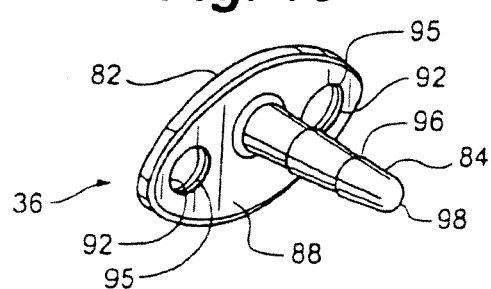
FIG. 19 is a perspective view from a second angle of the carpal plate in accordance with the present invention.

Carpal stem 84 extends outwardly from bone interface surface 88 a distance E and has a diameter D2 at its proximal end, having a smooth or stepped taper to D1 at its distal end. Preferably, carpal stem 84 is generally perpendicular to plate 82. Carpal stem 84 may include retaining ridges 96 and hemispherical end 98. Referring particularly to FIGS. 16-17 and 19, note that carpal stem 84 may be offset from a line connecting screw holes 92 a distance G. Carpal stem 84 is of a length E such that it does not extend into or beyond the carpal-metacarpal interface.

Ball 86 is secured against secondary articular surface 90. Preferably, plate 82, carpal stem 84 and ball 86 are integrally formed or machined from a single piece of material. Ball 86 is spheroidal in shape and has a diameter larger than that of ball support 100. Ball 86 is located generally between screw holes 92 to fall, when implanted, along an axis generally aligned with the third metacarpal. The diameter of ball 86 is equal to or slightly smaller than spheroidal portion 80 of socket 74 of carpal ball 34.

Carpal plate 36 is advantageously fabricated from cobalt chrome-molybdenum alloy material. Buttress surface 88 and carpal stem 84 may be coated with commercially pure titanium plasma coating to promote osseointegration. As mentioned above, carpal stem 84 is dorsally offset from screw holes 92 to accommodate the arch of the carpus. Secondary articular surface and ball 86 along with ball support 100 are precision machined and highly polished to allow smooth articulation with carpal ball 34.

Figure 9:
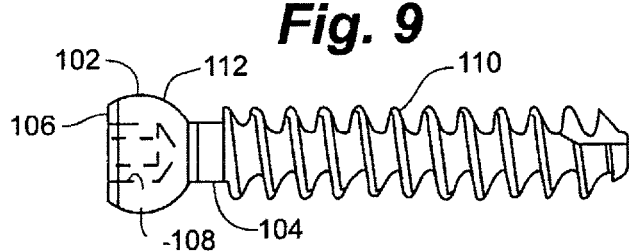
FIG. 9 is a plan view of a carpal screw in accordance with the present invention.
Figure 10A:
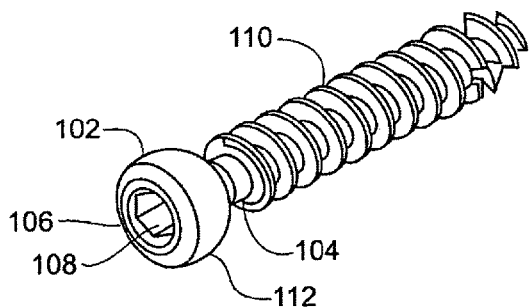
FIGS. 10a and 10b are perspective views of two carpal screws in accordance with the present invention.
Figure 10B:
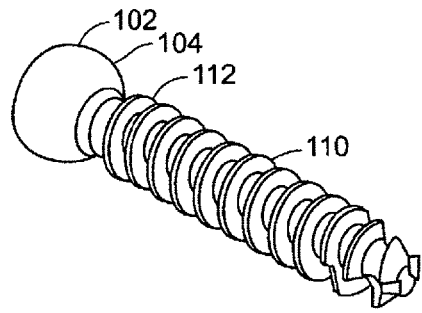
Figure 11:
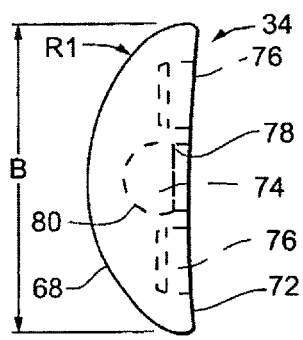
FIG. 11 is a plan view of a carpal ball in accordance with the present invention with phantom lines depicting internal structure.
Figure 12:
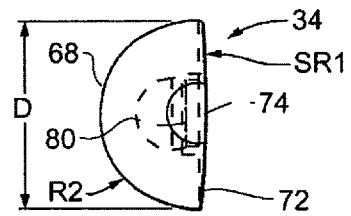
FIG. 12 is an elevational view of the carpal ball with phantom lines depicting internal structure.
Figure 13:
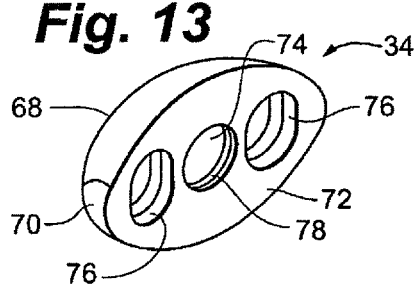
FIG. 13 is a perspective view of the carpal ball.
Figure 14:
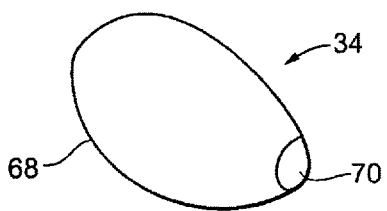
FIG. 14 is a second perspective view of the carpal ball in accordance with the present invention.
Figure 15:
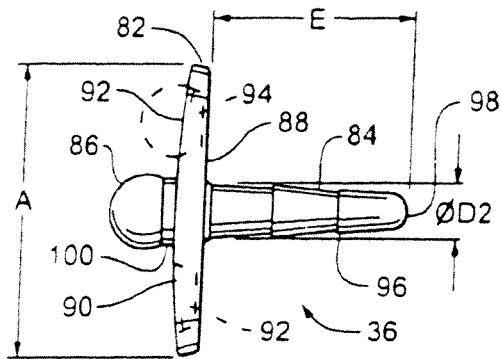
FIG. 15 is a plan view of a carpal plate in accordance with the present invention.

Referring particularly to FIGS. 9-10 and 21, carpal screws 38 generally include head 102 and shaft 104. In one embodiment, head 102 is spheroidal in shape and defines flat face 106 and driver interface 108. Driver interface 108, as depicted, accepts a standard 2.5 mm hex screwdriver but can be formed to interface with any screwdriver known in the art. Carpal screws 38 are selected of a length so that carpal screws 38 do not cross the carpal-metacarpal joint when implanted.

Shaft 104 may be of a length and diameter desired within the above limitations and has a cancellous thread form 110 for optimum fixation with the carpal bones of the wrist. An unthreaded portion of shaft 104 provides clearance so that carpal screws 38 may conically rotate relative to carpal plate 36. Spheroidal portion 112 of head 102 allows for ideal screw angulation as determined by a surgeon during the surgical procedure. Preferably carpal screws 38 are placed into the scaphoid and hamate bones of the carpus. The radius of spheroidal portion 112 is equivalent to that of spheroidal countersink 94 of carpal plate 36. Spheroidal portion 112 stands proud of secondary articular surface 90 of carpal plate 36 when implanted.

Carpal screws 38 are fabricated from cobalt chrome-molybdenum alloy material. Cancellous thread form 110 is designed to provide a secure grip in the cancellous and cortical portions of the carpal bones. Carpal screws 38 may be fluted for self-tapping application. The length of carpal screws 38 may vary as needed to accommodate patient anatomy but advantageously should not pass into or through the carpal-metacarpal joint. Carpal screws 38 may be manufactured to the standards of ISO 5835.

Figure 27:
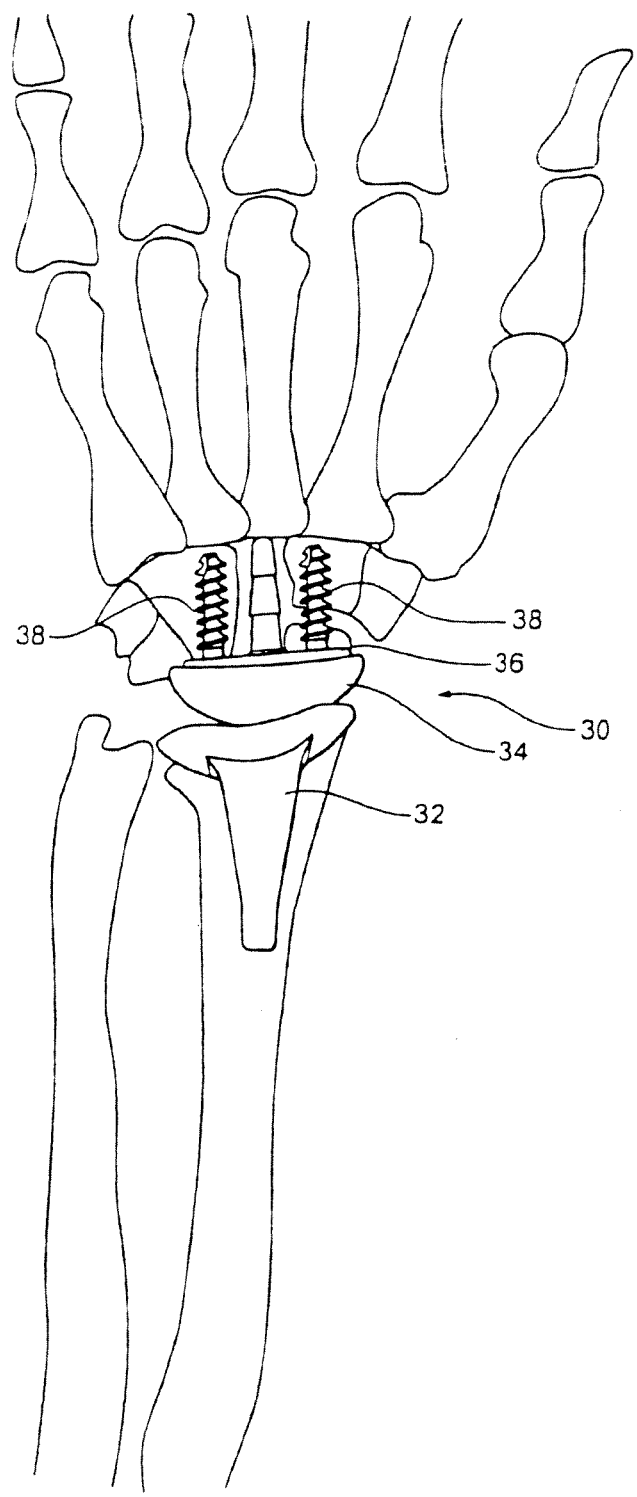
FIG. 27 is a schematic of the prosthetic wrist implant as implanted in a human wrist.

In operation, wrist implant 30 is implanted in the wrist of a patient to replace damaged or degenerated wrist structure as depicted in FIG. 27. In general, radius component 32 is implanted in the distal end of the radius without the need to perform resection of the distal portion of the radius. The distal radius cartilage and any heterotopic bone or osteophytes are removed from the scaphoid and lunate fossae at the end of the distal radius, but the bony structures of the distal radius preferably are not resected at all. A starter hole is drilled in the distal radius generally parallel to the long axis of the radius. This drilled hole provides a starting point for the use of a series of progressively larger broaches until the cavity in the distal radius is large enough to allow full seating of the radius component 32. The cavity is broached until it is large enough to provide a press fit for intra-medullary stem 46.

Prior to resecting the carpus, a guide (not shown) is used to measure the carpal resection. The bones of the carpus are resected across the proximal carpal row. Preferably, the carpal resection is performed along a plane generally perpendicular to the long axis of the radius. The lunate, triquetrum and proximal scaphoid and the head of the capitate may be resected. However, preferably only the lunate and the proximal pole of the scaphoid are removed. After the carpal bones are resected, a second guide (not shown) is temporarily attached to the carpal bones in order to allow for accurate drilling into the center of the capitate to provide a starter hole for a cavity for carpal stem 84. In addition, two starter holes are created to accommodate the placement of carpal screws 38 into the carpus. The radius component 32, carpal ball 34 and carpal plate 36 are then articulated. To articulate carpal ball 34 to carpal plate 36, carpal ball 34 is pressed against ball 86 so that socket 74 overlies ball 86. Force is then applied so that UHMWPE of carpal ball deforms around ball 86 and resiliently snaps back to grip ball 86.

The foregoing provides an overview of the surgical implantation procedure. A detailed description of the surgical procedure can be found below.

Once implanted, radius component 32 articulates with carpal ball 34 to provide a simulation of natural motion of the wrist. The toroidal shape of articular cup 48 and ellipsoidal shape of convex articular surface 68 interact to provide a free and natural primary articulation of wrist implant 30. Primary articulation 40 preferably allows a minimum radial deviation of about twenty degrees and an ulnar deviation of twenty degrees for a total of about forty degrees. Primary articulation 40 further allows extension of the wrist at least forty degrees and flexion of the wrist at least forty degrees for a total of about eighty degrees minimum. Note that the wrist implant 30 of the invention as depicted and disclosed herein permits much greater free movement of the wrist than these minimums. These minimum deviations have been found to provide a good range of motion for normal daily activities.

Thus, the motion of the implanted wrist implant 30 is generally hinged dorso-palmarly and gliding radio-ulnarly emulating normal joint kinematics. Flexion and extension occur about a first axis of rotation and radio-ulnar motion occurs about a second axis of rotation. In one embodiment of the invention, radius component 32 articulates with carpal ball 34 with a degree of incorporated laxity in the rotational degree of freedom. This incorporated laxity reduces torsional stresses that might otherwise be transferred to the bone-implant interfaces and tend to cause loosening of radius component 32 or carpal plate 36.

In one embodiment of the invention, radius component 32 articulates with carpal ball 34 in radial-ulnar deviation, flexion-extension and also in a rotational degree of freedom. As discussed above, convex articular surface 68 may be generally ellipsoidally shaped to interface with the toroidal shape of articular surface 64 of articular cup 48 to provide a close sliding fit therewith near the center of convex articular surface 68 but a looser sliding fit near articular ends 70. This interface allows carpal ball 34 to "wobble" relative to articular cup 48 thus providing limited rotational movement about an axis generally along the long axis of the radius. The use of ellipsoidal-toroidal geometry demonstrates constant line to line contact in the anterior-posterior and lateral planes.

Carpal ball 34 articulates with carpal plate 36 at secondary articulation 42. Socket 74 is an interference fit with ball 86. This secondary articulation 42 provides for motion about a rotational axis generally parallel to the long axis of the third metacarpal. Secondary articulation 42 provides for more natural wrist motion and lessens the risk of loosening of carpal plate 36 from the carpus and radius component 32 from the radius by minimizing the application of torsional forces to the bone-implant interfaces. The spheroidal head 102 of carpal screws 38 limits secondary articulation 42 by the interaction of oval excavation 76 with head 102 of carpal screws 38. Preferably, this limitation of movement is to about plus or minus five degrees or a total of about ten degrees.

Figure 18:
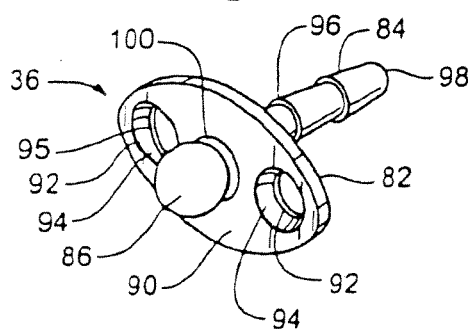
FIG. 18 is a perspective view of the carpal plate in accordance with the present invention.

Tertiary articulation 44 arises between the head 102 of carpal screws 38 and spheroidal countersink 94 in carpal plate (FIG. 18). Tertiary articulation 44 allows the surgeon to angle carpal screws 38 as desired for best fixation in bony structures while at the same time assuring that carpal screw 38 will have a tight interface with spheroidal countersink 94. Tertiary articulation preferably allows about ten to fifteen degrees of variation in the angle of carpal screws in any direction from a perpendicular to buttress surface 88.

Surgical Technique

A pre-operative assessment using an x-ray template should be made to approximate the size of the wrist implant 30. A carpal cutting guide may be provided with a small, medium, and large flange that can be fitted over the guide handle and tightened in place. Based upon an x-ray assessment, the appropriate size carpal resection guide should be assembled. The guide flange of the carpal resection guide is placed against the distal surface of the radius in the lunate fossa and the amount of carpal bone resection required is determined.

Dorsal Longitudinal Incision

A dorsal incision is made in line with the third metacarpal centered directly over Lister's tubercle.

Extensor Retinaculum Exposure

The extensor retinaculum is exposed and reflected from radial to ulnar from the first extensor compartment to the fifth or sixth extensor compartment.

A midline incision over the fourth extensor retinaculum is acceptable in "dry" rheumatoids and post-traumatic or osteoarthritic wrist. The distal part of the extensor retinaculum can be used to reinforce the dorsal wrist capsule in synovitic rheumatoid wrist.

Synovectomy of Extensor Tendons

After exposure, a synovectomy of the extensor tendons is performed as necessary.

Exploration of Carpals

A rectangular shaped wrist carpal flap is reflected from proximal to distal to expose the proximal and distal carpal rows. Synovectomy of wrist is performed as required.

Carpal Resection

A carpal resection guide (not shown) is set across the wrist joint for resection of the proximal carpal row. The length of the resection is determined by placing the flange against the distal radius/lunate fossae without carpal dislocation. The lunate, triquetrum, proximal scaphoid, and head of the capitate are resected.

Proximal Guide Placement

A proximal radial guide (not shown) is inserted to determine the resection of heterotopic bone and osteophytes from the distal radius. The convex side of the guide is placed against the concave surface of the distal radius. The wrist is flexed to allow best alignment of the proximal guide.

Drilling of the Radius

A radial template (not shown) in small, medium, and large sizes with left and right hand configurations is utilized. The proper template to be used is based upon the preoperative assessment. The distal face of the template represents the distal extent and peripheral coverage of the radial implant component. A drill hole in the template establishes a starting location for a broach. A 3.5 mm drill is inserted into the hole and a hole is drilled to a depth of 20-30 mm. The drill should be aligned along the long axis of the radius in both anterior/posterior and lateral planes. Biplanar fluoroscopic X-ray imaging confirmation of guide placement is important to insure proper alignment prior to broaching.

Preparation of the Radius

Based upon the pre-operative assessment of the implant size, the distal radius is broached with increasing sized broaches to allow full seating of the radius component 32. Care should be taken to ascertain that the handle of the broach is aligned with the long axis of the radius. The broach may need to be withdrawn occasionally to clean the teeth and clear the intra-medullary cavity of debris.

The goal is to remove no more subcortical bone than necessary to allow prosthesis insertion (resection of the distal radius, as is performed with other wrist prostheses, is not required or recommended).

Radial Trial Placement

A trial radius component 32 is inserted into the prepared canal and impacted. The fit of the radius component 32 against the scaphoid and lunate fossae is evaluated. If the fit is satisfactory, the trial radius component 32 is removed by engaging the extraction holes with a clamp. In some situations, it may be necessary to use a small burr to contour the cartilage of the radius to achieve a desired fit. The radial template (not shown) can be used as a guide to approximate the amount of burring needed.

Carpal Templating

A carpal template (not shown) for locating the carpal plate 36 fixation holes for receiving carpal screws 38 is placed against the distal carpal resection site. A central hole in the template is aligned with the center of the capitate. Biplanar imaging can be used to confirm proper alignment. Using k-wire(s), the distal pole of the scaphoid may be temporarily fixed to the capitate to facilitate scaphoid screw preparation and insertion.

Carpal Drilling

A 3.5 mm drill is inserted into the central hole and a hole is drilled through the capitate but not into the second or third metacarpal. Imaging can be used to confirm proper alignment. The hole is drilled to depths appropriate for the size of the implant utilized. The drill bit is preferably disconnected from the drill driver and left in place facilitate drilling of the radially and ulnarly positioned screw sites. A 0.62 k-wire is inserted into the ulnarly located hole of the carpal template. The k-wire can be angulated within the carpal template to achieve proper placement within the distal carpal row. The k-wire is drilled to the depth of the screw length determined pre-operatively and the drill is removed from the k-wire. Imaging can be performed to evaluate placement. The same procedure is repeated for the radially positioned hole of the carpal template. If the guide is aligned correctly, the k-wires and drill bit should form a "W" shape within the distal carpal row.

Carpal Trial Placement

The stem of the trial carpal plate 36 is inserted into the capitate verifying that the dorsal aspect of the trial component is positioned correctly. Note: the stem is offset dorsally from the screw holes to accommodate the natural arch of the carpus. The trial carpal plate is seated against the resection using a carpal impactor (not shown). Placement is confirmed with imaging.

Radial Trial Placement

The trial radial component 32 is placed into the radius and tapped into place using an impactor (not shown).

Carpal Ball Trial Placement

A carpal ball 34 trial component is placed over the trial carpal plate 36 and the joint is reduced. Note: preferably the carpal balls 34 are available in two thicknesses, neutral and plus.

Range of Motion Assessment

The joint is articulated and joint stability and motion are assessed. There should be slight distraction across the implant interface of no more than 2-3 mm. The cut generated by the carpal resection guide is designed for the neutral thickness of the carpal ball 34. However, if there appears to be too much joint laxity, the plus thickness carpal ball 34 can be used. It is very important that the proper carpal ball 34 size is selected because it is difficult to disarticulate the carpal ball 34 from the carpal plate 36 once assembled. Full range of motion without impingement or instability should be present. Once range of motion is satisfactory, all trial components should be removed.

Component Placement

The definitive radius component 32 and carpal plate 36 and carpal ball 34 are now inserted. The radius component 32 is designed for press fit, however bone allograft can be added if there is osteopenia or osteoporosis and to adjust seating of the radius component 32 to make up for any joint laxity. The radius component 32 is tapped firmly into place. Optionally, bone cement can be used to secure the radius component 32. The carpal plate 36 is inserted next. It is aligned with the centering hole in the capitate and pushed or tapped into place. The self-tapping radial and ulnar cancellous carpal screws 38 are inserted through the carpal plate 36 and into the holes created by the k-wires. The screws are now tightened into place.

The carpal ball 34 is snapped into place using the carpal ball impactor (not shown). The radius component 32 and carpal plate 36 are reduced and articulated. Any temporary scaphoid to capitate k-wires are removed. If indicated, bone graft from excised carpal bones can be used to fuse together the distal carpal bones.

If the carpal ball 34 needs to be removed, care must be taken to not damage the polished secondary articular surface 90 of the carpal plate 36. Removal may be necessary to adjust joint tension or laxity or to modify screw length. This can be accomplished by drilling a small hole in the radial and ulnar flattened articular ends 70 of the polyethylene and engaging the holes created with a bone reduction forceps and prying in a radial or ulnar direction to disengage the snap fit assembly.

Repair of Dorsal Capsule & Closure

The dorsal capsule is repaired back to the distal radius. If necessary drill holes are made in the dorsal, and distal radius. A tight capsule closure is performed with the wrist in extension (20°). A distal third of extensor retinaculum is added to reinforce capsular closure. Lastly, the extensor retinaculum is closed.

The present invention may be embodied in other specific forms without departing from the central attributes thereof, therefore, the illustrated embodiments should be considered in all respects as illustrative and not restrictive, reference being made to the appended claims rather than the foregoing description to indicate the scope of the invention.

What is claimed is:

1. An implantable wrist prosthesis for implantation in a patient's wrist, the patient's wrist including a distal end of a radius bone presenting a substantially concave end surface contour and a carpus, the implantable wrist prosthesis comprising:
   a radius component comprising an articular receiver and an intramedullary stem extending from the articular receiver, the articular receiver having an inner receiver wall and further having an outer receiver wall with a convex curvature adapted to substantially conform to a curvature of the concave end surface bone at an unresected distal end of the patient's radius bone, the outer receiver wall having a major curvature along a major dimension and a minor curvature along a minor dimension;
   a carpal plate having a bone interface surface, an articular surface opposite the bone interface surface, a first hole for receiving a first carpal screw, a second hole for receiving a second carpal screw; and
   a carpal piece for positioning between the radius component and the carpal plate, the carpal piece including a back surface configured to articulate relative to and in engagement with the articular surface of the carpal plate about a rotational axis.

2. The implantable wrist prosthesis of claim 1, further comprising a carpal stem extending from the bone interface surface at a location offset from an axis connecting the centers of the first hole and the second hole.

3. The implantable wrist prosthesis of claim 1, wherein the carpal plate is configured to allow angular articulation of the first and second carpal screws when the first and second carpal screws are received in the first and second holes.

4. The implantable wrist prosthesis of claim 1, wherein the articular surface of the carpal plate is convexly curved, and wherein the back surface of the carpal piece is concavely curved.

5. The implantable wrist prosthesis of claim 1, wherein the back surface of the carpal piece defines a first excavation configured to interact with the first carpal screw and a second excavation configured to interact with the second carpal screw.

6. The implantable wrist prosthesis of claim 5, wherein the carpal plate further includes a protrusion extending from the articular surface, and wherein the back surface of the carpal piece further defines socket between the first excavation and the second excavation configured to receive the protrusion along the rotational axis.

7. The implantable wrist prosthesis of claim 5, wherein articulation of the carpal plate with respect to the carpal piece is limited by an interaction of the first and second carpal screws with the first and second excavations.

8. An implantable wrist prosthesis for implantation in a patient's wrist, the patient's wrist including a distal end of a radius bone presenting a substantially concave end surface contour and a carpus, the implantable wrist prosthesis comprising:
   a radius component comprising an articular cup and an intramedullary stem extending from the articular cup, the articular cup having an inner cup wall and further having an outer cup wall with a convex curvature adapted to substantially conform to a curvature of the concave end surface contour at an unresected distal end of the patient's radius bone, the outer cup wall having a major curvature along a major dimension and a minor curvature along a minor dimension;
   a carpal plate having a bone interface surface and an articular surface opposite the bone interface surface; and
   a carpal piece for positioning between the radius component and the carpal plate, the carpal piece configured to demonstrate line-to-line contact with the articular cup in the anterior-posterior and lateral planes when the implantable wrist prosthesis is implanted in the patient's wrist, the carpal piece including a back surface configured to articulate relative to and in engagement with the articular surface of the carpal plate about a rotational axis.

9. The implantable wrist prosthesis of claim 8, wherein the carpal plate is configured to receive a carpal screw at variable angles relative to the carpal plate when implanted.

10. The implantable wrist prosthesis of claim 9, wherein the back surface of the carpal piece defines an excavation configured to interact with the carpal screw.

11. The implantable wrist prosthesis of claim 10, wherein articulation of the carpal plate with respect to the carpal piece is limited by an interaction of the carpal screw with the excavation.

12. The implantable wrist prosthesis of claim 8, wherein the articular surface of the carpal plate is convexly curved, and wherein the back surface of the carpal piece is concavely curved.

13. The implantable wrist prosthesis of claim 8, wherein the carpal plate further includes a protrusion extending from the articular surface, and wherein the back surface of the carpal piece further defines socket configured to receive the protrusion along the rotational axis.

14. An implantable wrist prosthesis comprising:
   a radius component configured as a surface replacement arthroplasty for an unresected distal end of a patient's radius bone, the radius component comprising:
     an articular cup having a major dimension and a minor dimension, the articular cup including an inner cup wall and an outer cup wall, the outer cup wall having an exterior surface with a convex curvature substantially conforming to a curvature of a concave end surface of the unresected distal end of the patient's radius bone, the exterior surface having a major curvature along the major dimension and a minor curvature along the minor dimension; and
an intramedullary stem integral with the articular cup and extending outwardly from the outer cup wall; and
a carpal component securable to a carpus; and a carpal piece between the radius component and the carpal component, the carpal piece engaging into the inner cup wall and having at least two degrees of freedom relative to the articular cup, the carpal piece engaging the carpal component and having limited rotational freedom relative to the carpal component, the carpal piece engaging the carpal component via an interference fit between a generally spheroidal protrusion and a generally spheroidal socket.

15. The implantable wrist prosthesis of claim 14, wherein the convex curvature of the exterior surface conforms to a curvature of the scaphoid and lunate fossae of the radius bone.

16. The implantable wrist prosthesis of claim 14, wherein the inner cup wall includes a concave articular surface having a major radius and a minor radius.

17. An implantable wrist prosthesis comprising: a radius component configured as a surface replacement arthroplasty for an unresected distal end of a patient's radius bone, the radius component comprising: an articular cup having a major dimension and a minor dimension, the articular cup including an inner cup wall and an outer cup wall, the outer cup wall having an exterior surface with a convex curvature substantially conforming to a curvature of a concave end surface of the unresected distal end of the patient's radius bone, the exterior surface having a major curvature along the major dimension and a minor curvature along the minor dimension; and an intramedullary stem integral with the articular cup and extending outwardly from the outer cup wall; and
a first carpal screw having a head and a shaft;
a second carpal screw having a head and a shaft;
a carpal plate having a bone interface surface, an articular surface opposite the bone interface surface, a first hole configured to receive the first carpal screw such that head of the first carpal screw extends beyond articular surface and the shaft of the first carpal screw extends beyond the bone interface surface when implanted, and a second hole configured to receive the second carpal screw such that the head of the second carpal screw extends beyond the articular surface and the shaft of the second carpal screw extends beyond the bone interface surface when implanted; and
a carpal piece having a back surface configured to rotate relative to and in engagement with the articular surface about a rotational axis, the back surface including a first excavation for receiving the head of the first carpal screw and a second excavation for receiving the head of the second carpal screw when implanted, an interaction of the heads of the first and second carpal screws with the first and second excavations providing a limit to the rotation of the carpal plate relative to the carpal piece about the rotational axis.

* * * * *